United States Patent [19]
Harper

[11] Patent Number: 6,087,296
[45] Date of Patent: Jul. 11, 2000

[54] RANEY IRON CATALYST AND A PROCESS FOR HYDROGENATING ORGANIC COMPOUNDS USING SAID CATALYST

[75] Inventor: Mark Jay Harper, Middletown, Del.

[73] Assignee: E. I. du Pont de Nemours & Co., Wilmington, Del.

[21] Appl. No.: 09/186,987

[22] Filed: Nov. 5, 1998

[51] Int. Cl.$^7$ .......................... B01J 25/00; C07C 255/04
[52] U.S. Cl. .......................... 502/301; 502/326; 558/452; 558/459; 560/205; 562/598; 564/491; 568/382; 568/445
[58] Field of Search .................................... 502/301, 326; 558/452, 459; 560/205; 562/598; 564/491; 568/382, 445

[56] References Cited

U.S. PATENT DOCUMENTS

| | | | |
|---|---|---|---|
| 2,257,814 | 10/1941 | Rigby | 260/464 |
| 4,544,749 | 10/1985 | Tadashi et al. | |
| 4,826,799 | 5/1989 | Cheng et al. | 502/301 |
| 4,895,994 | 1/1990 | Cheng et al. | 585/270 |
| 5,151,543 | 9/1992 | Ziemecki | 558/459 |

FOREIGN PATENT DOCUMENTS

| | | |
|---|---|---|
| WO 97/37963 | 4/1997 | WIPO. |
| WO 9843941 | 10/1998 | WIPO. |

OTHER PUBLICATIONS

L. Kh. Freidlin, Academician A. A. Balandin and T.A. Sladkova, Preparation of p–Xylylenediamine By Catalytic Reduction of Terephthalonitrile, N.D. Zelinsky Institute of Organic Chemistry, Academy of Sciences, USSR, Chemistry Index, 1957, vols. 112–117, pp. 141–142, Jan–Dec.

L. Kh. Freidlin and T.A. Sladkova, Catalytic Reduction of Dinitriles, Russian Chemical Reviews, vol. 33, No. 6, Jun. 1964.

Robert L. Augustine, Catalytic Hydrogenation, Techniques and Applications in Organic Synthesis, 1965, Marcel Dekker, Inc. New York.

*Primary Examiner*—Joseph McKane
*Assistant Examiner*—Joseph Murray
*Attorney, Agent, or Firm*—Shanks & Herbert

[57] ABSTRACT

The present invention relates to a Raney catalyst comprising iron, cobalt, a third metal wherein the third metal is selected from the group consisting of nickel, rhodium, ruthenium, palladium, platinum, osmium, iridium and mixtures of any of these metals.

19 Claims, 4 Drawing Sheets

RANEY IRON CATALYST AND A PROCESS FOR HYDROGENATING ORGANIC COMPOUNDS USING SAID CATALYST

The present invention concerns a novel Raney iron catalyst, its preparation and process for its use in the catalytic hydrogenation of unsaturated organic groups including groups having carbon-carbon multiple bonds, oxygen-containing groups and reducible nitrogen-containing groups, particularly nitriles. More specifically, but not by way of limitation, the present invention provides an improved catalyst and process for hydrogenation of adiponitrile (ADN) to 6-aminocapronitrile (ACN) and hexamethylenediamine (HMD).

BACKGROUND OF THE INVENTION

Raney metal catalysts containing iron have been reported, but these catalysts showed poor results in hydrogenation reactions. For example, it was reported in L. Kh. Freidlin, A. A. Balandin, and T. A. Sladkova in Dokl. Akad. Nauk SSSR, 112, 880 (1957) that attempted hydrogenation of the dinitrile of terephthalic acid in the presence of Raney iron as catalyst gave no isolatable diamine. Later, in L. Kh. Freidlin and T. A. Sladkova, Russ. Chem. Rev., 33, 319 (1964) it was stated "Raney iron has a low catalytic activity" and "activity of metallic catalysts towards the reduction of dinitriles decreases in the sequence: Pt,Pd>Ni>Co>Fe,Cu." In R. L. Augustine, *Catalytic Hydrogenation*, Dekker, N.Y., 1965, p. 32, it is stated "Raney copper and Raney iron do not have much to offer the synthetic organic chemist, as only a few reactions are reported to be affected by them".

U.S. Pat. No. 2,257,814 describes hydrogenation of dinitriles in the presence of mild-acting catalysts prepared by leaching an alloy of aluminum, iron and cobalt with an aqueous alkaline solution to provide the catalyst which contains 5 to 10% by weight of cobalt and 95 to 90% by weight of iron. The use of third metal in catalyst compositions taught in this patent is discouraged.

U.S. Pat. Nos. 4,826,799 and 4,895,994, each directed to catalysts made by the Raney process and pelletized in a matrix of polymer and plasticizer, make a broad disclosure of Raney process alloys consisting of 45–75 weight % Al and 25–55% of a conventional Raney process metal, e.g., Ni, Co, Cu, or Fe, or mixture of these. These Raney catalysts may be promoted by, e.g., Cr, Mo, Pt, Rh, Ru, Os and Pd, typically at about 2 weight % of total metal.

U.S. Pat. No. 5,151,543 reports a process for selective hydrogenation of aliphatic dinitriles to aminonitriles under low pressure with high yield using a Raney-type catalyst selected from the group consisting of Raney nickel, Raney cobalt, and Raney nickel promoted with metals or metal oxides selected from Group VIB or promoted with ferrous metals of Group VIII of the Periodic Table. Thus, in this catalyst iron, if used at all, would be present in only low concentrations.

It is an object of the present invention to provide a Raney iron catalyst which is effective in the low pressure catalytic hydrogenation of a variety of organic compounds, particularly a catalyst effective for the hydrogenation of aliphatic organic nitrites to organic primary amines.

SUMMARY OF THE INVENTION

The present invention provides Raney iron catalyst comprising iron, cobalt and a third metal wherein the third metal is selected from the group consisting of nickel, rhodium, ruthenium, palladium, platinum, osmium, iridium and mixtures of any of the metals of this group and wherein the concentration of the iron in the catalyst on a dry basis is at least 30% but not more than about 70% by weight; the concentration of the cobalt in the catalyst on a dry basis is from at least 10 to 40% by weight; the content of the third metal in the catalyst on a dry basis is from about 1 to not more than 6% by weight. Nickel is the preferred third metal and the preferred catalyst has the following metal concentrations: iron about 50% by weight; cobalt about 15% by weight; nickel is about 2% by weight.

The present invention includes a process for the hydrogenation of unsaturated organic compounds comprising contacting an unsaturated organic compound with the Raney iron catalyst of this invention in the presence of hydrogen at a reaction pressure of from 50 to 2000 psig (13.78 MPa) and at a reaction temperature of from 25 to 150° C.

This process is useful in hydrogenating unsaturated organic compounds selected from the group consisting of olefins, acetylenes, ketones, aldehydes, amides, carboxylic acids, esters of carboxylic acids, nitro compounds, nitriles, and imino compounds. This process is particularly useful in the hydrogenation of nitrites, especially adiponitrile.

The present process is useful at moderate conditions: a reaction pressure from about 50 to about 1000 psig (6.89 MPa) and a reaction temperature from about 25 to about 80° C.

The present process may be run as a continuous, semi-batch or batch process.

The catalyst of the present invention is prepared by treating an alloy of metals with alkali, the alloy comprising from 20 to 50% by weight iron, 3 to 30% by weight cobalt, 0.5 to 3% by weight of a third metal wherein the third metal is selected from the group consisting of nickel, rhodium, ruthenium, palladium, platinum, osmium, iridium and mixtures of any of the metals of this group with the remainder being an alkali soluble metal selected from the group consisting of aluminum, zinc, magnesium and silicon. Nickel is the preferred third metal, and the preferred concentration range for the nickel is the range from 0.5 to 1.5%. The most preferred concentration of nickel is about 1% or less. A preferred composition for the alloy is iron about 24 to 34%, cobalt about 5 to 15% and nickel about 0.5 to 1%.

DETAILED DESCRIPTION

Figure 1:
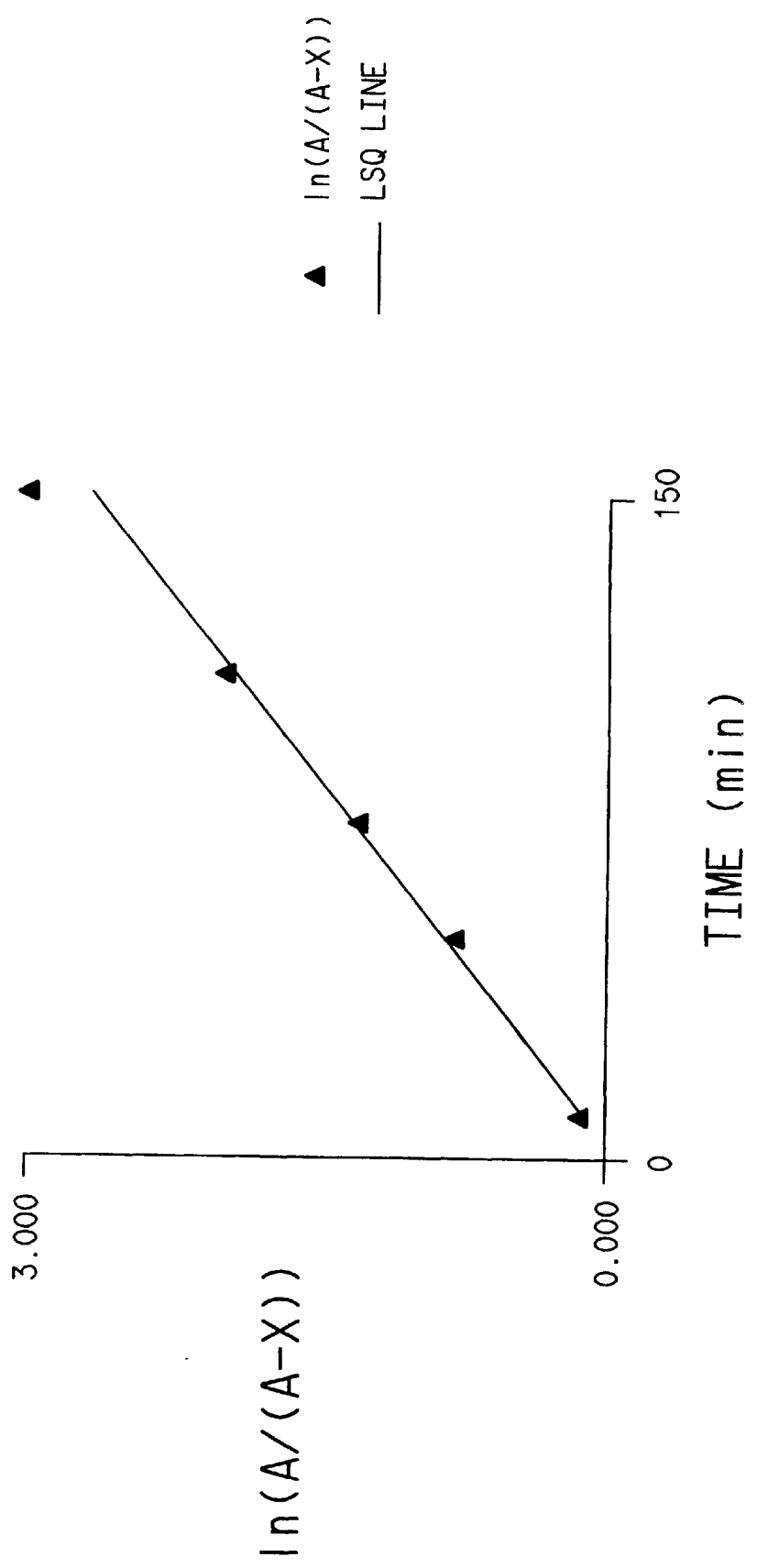
FIG. 1 shows the disappearance of ADN for the stable catalyst of Example 2 compared to the theoretical the first order rate line of the catalyst of Example 2.

The Raney iron catalysts of this invention are prepared by treating an alloy powder with an alkali, the composition of the alloy being, by weight: iron, 20% to 50%, cobalt, 3% to 30%, and 0.5% to 3% of a third metal wherein this third metal is selected from the group consisting of nickel, rhodium, ruthenium, palladium, platinum, osmium, iridium and mixtures of any of these metals. The remainder of the catalyst composition is a metal soluble in the alkali. The alkali soluble metals include aluminum, zinc, magnesium and silicon. Aluminum is the preferred alkali soluble metal, and nickel is the preferred third metal for the catalyst.

The alloy is prepared by the usual metallurgical procedures which produce alloy ingots. To obtain the alloy in the desired powder form, the ingot is crushed and ground. A sieved alloy powder having a particle size that will pass a 30 mesh screen is preferably used.

The alloy is converted to active catalyst, by treating it with a 10–30% by weight aqueous solution of an alkali metal hydroxide, preferably sodium hydroxide, at 50–110° C. When the alloy and alkaline solution have been mixed and hydrogen evolution has ceased (usually within two hours), the catalyst is thoroughly washed two or three times with deionized water. The resulting catalyst is normally stored under water to insure that it does not contact air. The metal contents of the active catalysts of the present invention on a dry basis are by weight from about 30% to about 70% iron, from about 5% to about 40% cobalt, from about 1% to about 6% nickel. The remainder of the catalyst composition depends on whether or not promoters have been added and on the thoroughness of the leaching process. Generally some small amount of aluminum will remain in the catalyst. Also since the analysis is done on the dry catalyst, some oxides are present. The numbers above have been normalized to oxide-free data.

Raney catalysts consisting of iron and cobalt have been reported as have catalysts consisting of iron and nickel. The inventor of the present invention has found that cobalt and iron combinations produce a stable catalyst; while combinations of iron and nickel produce an active catalyst. While the activity of the iron/nickel combination is much desired, this combination also is short-lived and deactivates at a rate that is too rapid for commercial processes. The inventor has found that a combination of the three metals within precise concentration ranges produces both an active catalyst and stable catalyst. The catalysts of the present invention are formulated in this precise concentration range and have surprisingly the activity of the iron/nickel combination with stability equal to or better than the iron/cobalt combination. To achieve the advantage of the catalyst of this invention, the concentration of cobalt in the alloy may be as much as 15% and the concentration of nickel may be as much as 6%. The present invention requires that the concentration of cobalt in the alloy must be at least 5% and is preferred to be at least about 9%; while the concentration of the nickel in the alloy must be 0.5% and is preferred to be less than 1.5%.

The inventor has found that other metals may be used to replace the nickel in the catalyst of the present invention. These other metals are rhodium, ruthenium, platinum and a mixture of platinum and ruthenium. The preferred mixture of platinum and ruthenium is 90% by weight platinum. While the concentrations of these metals with the iron and cobalt that achieve maximum activity and stability may differ from those of nickel and from each other; these concentrations fall within the range of from about 0.5 to 6% in the alloy.

Unlike earlier reported Raney catalysts, the catalysts of the present invention require a combination of three metals. Promoters may also be incorporated into the present catalysts. Such promoters include the known promoters for Raney catalysts.

The catalysts of this invention are used for promoting the reaction of hydrogen with organic compounds which contain unsaturated groups. The unsaturated groups include olefinic groups; acetylenic groups; carbonyl in ketones, aldehydes, amides, carboxylic acids and esters; nitro; imino; and nitrile groups. The catalysts of the present invention may also be used for reduction of alcohols, for hydrogenolysis of sulfur-containing organic compounds and for Fischer-Tropsch reaction.

The catalysts of the present invention are particularly useful for hydrogenation of nitriles. In the hydrogenation of nitrites, the present catalysts minimize process costs because low pressures—in the range of about 50 psig (0.345 MPa) to about 2000 psig 13.78 MPa) may be used, and the hydrogenation proceeds well at temperatures from about 25° C. to about 150° C. The preferred range of pressure for hydrogenation of nitriles using the catalysts of the present invention is from about 200 psig (1.38 MPa) to about 1000 psig (6.89 MPa), and the preferred temperature is from about 60° C. to about 80° C. Hydrogenations according to the present invention generally do not require the presence of caustic soda or other strong alkali.

Hydrogenation according to the present invention may be run in the presence of a solvent such as liquid ammonia, aqueous ammonia (as in Example 2), an aliphatic alcohol having one to four carbon atoms (as in Example 3) or an aliphatic hydrocarbon having four to ten carbon atoms. The presence of one or more solvents can improve the selectivity to aminonitriles in the hydrogenation of dinitriles. In the hydrogenation of adiponitrile (ADN), solvents in amounts greater than one mole per mole of dinitrile may be used, and it is preferred to use from about one mole to about five moles of solvent per mole of ADN.

The process of the present invention may be operated batchwise, semi-batchwise or continuously in an appropriate reactor. For commercial manufacture, the continuous process is preferred. In the hydrogenation of ADN to produce ACN and HMD the invention catalyst has a low deactivation rate and provides the stable reaction rate and distribution of products needed for a successful continuous commercial process.

Figure 3:
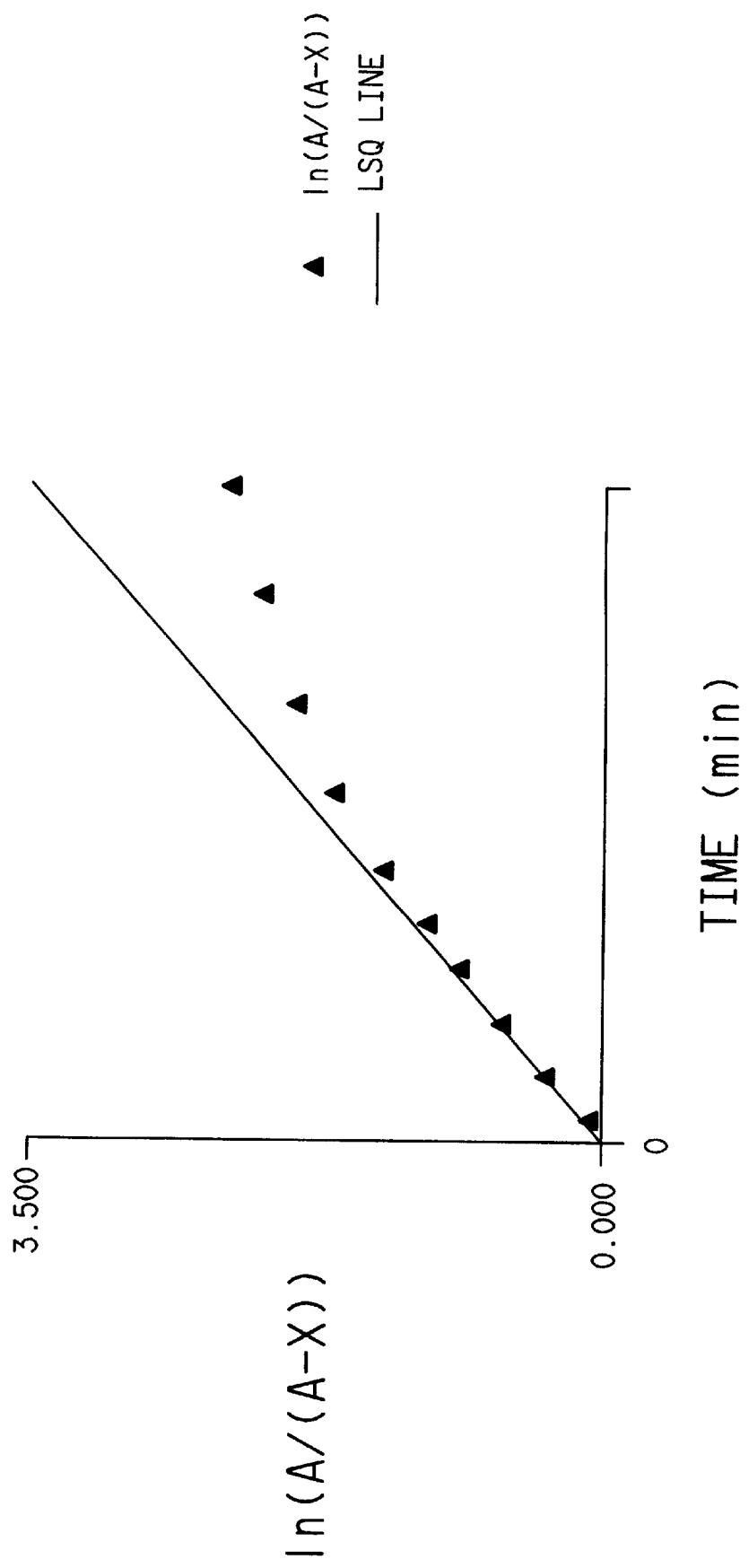
FIG. 3 shows the disappearance of ADN for the unstable catalyst of Example 6 compared to the theoretical the first order rate line.

The stability of a catalyst for potential use in a continuous hydrogenation of a nitrile can be assessed from rate data generated in a batch reaction. Thus, in the hydrogenation of adiponitrile, the reaction follows a first order rate relationship. Negative deviation with time from the first order rate pattern indicates deactivation (loss of stability) of the catalyst activity. Experimentally, the first order rate line is plotted using the least squares method based on the first few data points collected in the process run. When the experimental data points throughout the reaction are a good fit to this first order rate line, the catalyst is stable showing no deactivation as is illustrated in FIG. 1, but, when the plot of the experimental data points show a negative deviation (decreasing slope), deactivation of the catalyst has occurred. Catalyst deactivation is shown in FIG. 3. The catalysts of the present invention show outstanding stability as is shown in the Examples, below.

Reactors useful for performing continuous hydrogenation according to the present invention include, generally, any conventional hydrogenation reactor. Examples of such reactors include, but are not limited to, plug flow reactor, continuous stirred tank reactor, and bubble column reactor. An example of a bubble column reactor, which is not confined to this reaction, has been described in U.S. Pat. No. 4,429,159. Descriptions of plug flow and continuous stirred tank reactors have been delineated in the book entitled "Chemical Reaction Engineering" written by Octave Levenspiel.

The continuous hydrogenations of adiponitrile described below in Examples 3 and 4 were carried out in a continuous stirred tank reactor (CSTR), a 300 cc autoclave designed and fabricated by Autoclave Engineers. It was constructed of Hastelloy-C with a maximum allowable working pressure of about 1500 psig (10.34 MPA) at 300° C. Mixing in the reactor was performed with a magnetically coupled impeller, mounted on a hollow shaft and driven by an electric motor. The reactor was heated with a 400 Watt external band heater.

Because they give long term stability without deactivation in continuous operation, the preferred catalysts of this invention are those prepared from alloys containing, by weight, 25% to 45% iron, 5% to 15% cobalt, 0.7% to 1.5% nickel and the remainder being an alkali soluble metal such as aluminum. The nickel content is of particular importance since stability is lessened at concentrations of nickel higher than about 2%. The long term stability of the preferred catalyst composition made from an alloy containing 1% nickel is demonstrated by the continuous run of Example 3, while Example 7 demonstrates that a nickel content of 5% results in a less stable catalyst.

The present invention further provides a process for hydrogenation of an organic nitrile, comprising contacting the nitrile with gaseous hydrogen in the presence of a Raney iron catalyst prepared from a metal alloy containing by weight 20% to 50% iron, 3% to 30% cobalt, and 0.5% to 3% of a third metal wherein the third metal is selected from the group consisting of nickel, rhodium, ruthenium, palladium, platinum, osmium, iridium and mixtures of any of these metals; and subsequently agitating the nitrile, hydrogen, and catalyst to form a primary amine.

Although low pressure is preferred for the process of the present invention, the process may be run at higher pressures. Pressures of more than 2000 psig (13.78 MPa) could be used with the process and catalyst of this invention, but such high pressures may not be cost effective.

The following Examples illustrate the present invention, but are not intended to limit the invention.

EXAMPLES

EXAMPLE 1

This Example illustrates the preparation of a catalyst of the present invention where the third metal is nickel and the alkali soluble metal is aluminum.

Into a graphite crucible was placed 52.20 g of aluminum. The crucible was then placed in a quartz cup which was partially filled with popcorn quartz for insulation. The quartz cup with its contents was positioned inside the induction coil of an induction furnace. When the aluminum was melted, a mixture of 26.10 g iron chips, 7.83 g cobalt chips and 0.87 g nickel shot was carefully added to the molten aluminum. The resulting molten mixture was stirred with a graphite rod. The furnace was closed and the power turned on for 2 minutes. The furnace was opened, the melt was again stirred with the graphite rod, the furnace was closed again and power was applied for another 2 minute period. The power to the furnace was then turned off, and the furnace was opened. The graphite crucible with its molten contents was lifted from the quartz cup, and the molten metal alloy was poured from the graphite crucible onto a graphite cooling plate located inside the furnace. After the alloy had cooled and hardened for about 10 minutes, it was removed from the graphite cooling plate and cooled under water until it was at room temperature.

The cooled alloy was dried, crushed to provide pieces <5mm in their longest dimension and milled using one inch diameter steel balls in a planetary ball mill. The milled powder was screened using a 30 mesh sieve. The screened alloy powder was stored in a labeled container and is ready for activation.

The alloy was activated by first mixing 5 g of alloy powder with 50 g water followed by heating this mixture to about 85° C. with stirring. Sixty grams of a 50% by weight aqueous solution of sodium hydroxide was carefully added to the stirred alloy slurry, and stirring was continued at 90° C. for 30 minutes. Stirring was then stopped, and the catalyst was allowed to settle. The liquid was decanted, and the catalyst was washed with three 100 ml portions of deionized water. The resulting washed catalyst was added to 100 g of 5% by weight sodium hydroxide solution and the mixture was stirred at 90° C. for 30 minutes. The catalyst was separated from the liquid by decantating the liquid, and then it was washed with successive 100 ml portions of deionized water (usually about 5 portions) until neutral (pH 7 as measured with ColorpHast® pH 0–14 test paper from EM Science). The activated catalyst was stored under water.

The resulting catalyst when dried contains 51.1% iron, 15.4% cobalt, 2.0% nickel and 2.9% aluminum.

EXAMPLE 2

This Example illustrates the use of the catalyst prepared in Example 1 in the hydrogenation of adiponitrile.

A 100 ml Parr Instrument Company Hastelloy-C stirred autoclave was used for the hydrogenation. The autoclave reactor cup was charged with 2.0 g of wet catalyst prepared by the procedure of Example 1 and 26.2 g of 30% aqueous ammonium hydroxide. The reactor cup was secured to the reactor head, and the reactor was pressurized with 300 psig (2.07 MPa) nitrogen and then purged with hydrogen.

After the reactor contents were heated to 75° C. under 200 psig hydrogen pressure, a mixture of 10.8 g adiponitrile, 5.0 g methanol and 0.5 g 1-methyl-2-pyrrolidinone (NMP) was injected from a 75 ml addition cylinder under 500 psig (3.45 MPa) hydrogen pressure (the NMP was added as an internal standard for GC analysis).

The temperature of 75° C. and hydrogen pressure of 500 psig were maintained until hydrogen up-take was 81 psig as measured from a 1000 ml hydrogen supply reservoir. The reaction time was 312 minutes. The 81 psig hydrogen up-take was considered to signal the end of the reaction.

During the hydrogenation, samples (0.5 ml) of the reaction mixture were periodically withdrawn from the reactor and analyzed by GC in order to construct concentration profiles of the main reaction components.

At the end of the reaction, the reaction mixture was cooled to 20° C., the autoclave was vented, and the product was discharged.

The GC analysis data showed that the ADN conversion was 95% at 150 minutes. At 74% ADN conversion, 53% ACN and 9% HMD had formed; selectivity (defined as in Mares, et. al., J. Catal., 112, 145–156, 1988) to ACN was 72%. Byproduct concentration at 74% ADN conversion was about 4%; the byproducts comprise bis-hexamethylenetriamine and traces of hexamethyleneimine and tetrahydroazepine.

The first order reaction rate constant was 1.121 hr$^{-1}$. As shown in FIG. 1, the data points for the first order ADN disappearance fit the first order rate line indicating good catalyst stability.

EXAMPLE 3

This example illustrates the continuous hydrogenation of ADN.

A 300 cc continuous stirred tank reactor was used that was provided with a thermocouple insert, rupture disc, and two ⅛ inch dip legs fitted with 5 micron stainless steel frits, designed for liquid addition into the reactor and product withdrawal from the reactor, respectively.

The reactor was charged with 120 grams of methanol, 0.6 ml caustic solution (50% sodium hydroxide), and 15 grams of the wet activated catalyst (7.5 g dry weight) of Example 1.

The reactor was sealed, flushed with nitrogen several times and pressure tested at 1000 psig (6.89 MPa). After ensuring that there were no leaks, the reactor was heated to 75° C. and the agitator switched on (1200 rpm). As soon as the desired reaction temperature was achieved, the reactor pressure was set to 1000 psig by adjusting the back pressure regulator, and hydrogen was fed via the hollow shaft of the agitator. Hydrogen flow rate into the reactor was metered and monitored by a BROOKS mass flow controller. The hydrogen flow rate was set to 600 standard cubic centimeters per minute.

ADN and ammonia were then each continuously added to the reactor using ISCO syringe pumps at a rate of 12 grams per hour along with water at a rate of 1 gram per hour. Hold up time of the products in the reactor was 5.0 hrs.

Figure 2:
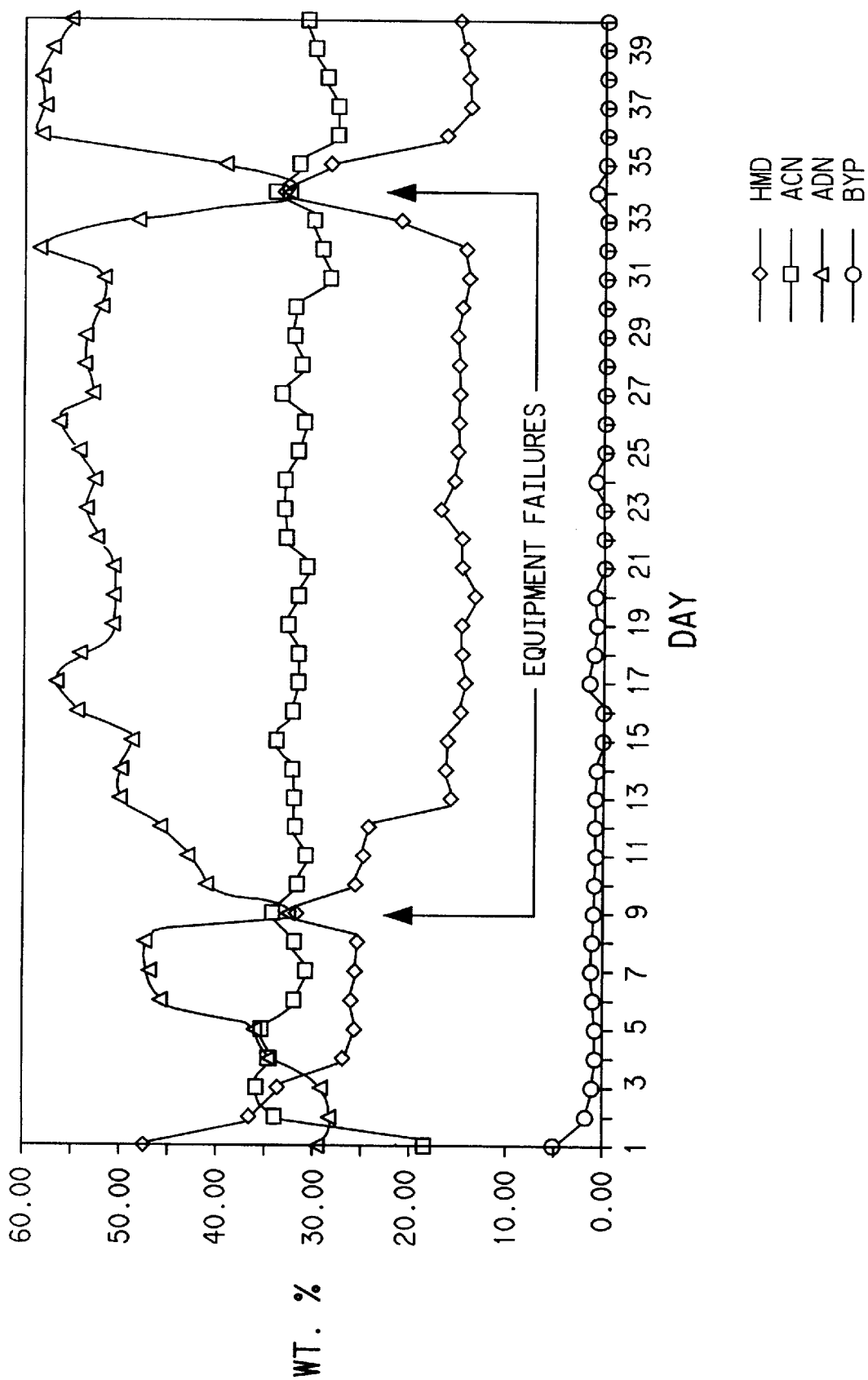
FIG. 2 shows the product distribution of the continuous run described in Example 3.

Product was collected in a one liter product receiver which was connected to the reactor through a let-down tank. As the reaction proceeded samples were taken at regular intervals and analyzed by GC for ACN, HMD, ADN and byproducts (BYP). The analytical results showing the production of ACN, HMD and BYP as a function of run time in days is presented in FIG. 2.

Except for upsets caused by equipment problems at about 166 hours and at 766 hours (see FIG. 2), the continuous hydrogenation proceeded in a stable manner for 937 hours (39 days), the end of the experimental run. At 668 hours the temperature was raised from 75° C. to 80° C. and at 716 hours the temperature was again raised to 90° C. and maintained at this temperature for the remainder of the run. At 80° C. and 90° C. the reaction continued to proceed essentially the same as at 75° C. Data from this continuous run are shown graphically in FIG. 2.

EXAMPLE 4

This Example illustrates the hydrogenation of n-butyronitrile.

The activated catalyst of Example 1 was used. The reactor procedure as described in Example 2 was employed using 1.00 g wet catalyst and 26.2 g of 30% aqueous ammonium hydroxide with a charge of 10.8 g n-butyronitrile, 0.50 g 1-methyl-2-pyrrolidone and 5.00 g methanol. The hydrogenation was conducted at 75° C. under a pressure of 500 psig (3.45 MPa) until the hydrogen uptake was 115 psig (0.79 MPa)(355 min).

Analysis of the reaction mixture by GC showed a yield of 73% n-butylamine along with byproduct yields of 2% di(n-butyl)imine and 2% di(n-butyl)amine. The first order reaction rate constant was 0.545 hr.$^{-1}$. The reaction rate followed the first order rate line for the 355 minutes of the reaction indicating no catalyst deactivation.

EXAMPLE 5

An alloy containing by weight 60 parts of aluminum, 38 parts of iron, and 2 parts of cobalt was prepared and was treated with aqueous sodium hydroxide to give the activated catalyst as described in Example 1 of U.S. Pat. No. 2,257,814.

ADN was hydrogenated in the presence of this activated catalyst according to the reactor procedure of Example 2. This reaction produced ACN and HMD, but the reaction rate was much slower than that observed in Example 2.

First order rate constant was only 0.088 hr.$^{-1}$ while with the invention catalyst it was 1.121 hr-$^{1}$. After a reaction time of 303 minutes ADN conversion was only 34% while with the invention catalyst of Example 1, ADN conversion was 95% after only 150 minutes.

EXAMPLE 6

Using the procedure of Example 1, an alloy consisting of, by weight, 60 parts aluminum, 30 parts iron, 5 parts cobalt, and 5 parts nickel was prepared. This alloy was then pulverized and converted to active Raney metal catalyst by treatment with aqueous sodium hydroxide.

ADN was hydrogenated using the above catalyst according to the procedure of Example 2. The reaction conditions of 75° C. and 500 psig (3.45 MPa) hydrogen pressure were maintained until hydrogen uptake was 145 psig as measured from a 500 ml hydrogen supply reservoir.

The reaction time was 320 minutes at which time ADN conversion was 90%. At 73% ADN conversion, 54% ACN and 12% HMD had formed. However, catalyst deactivation was noted starting at about 100 minutes of reaction time. This deactivation is shown by the decreasing slope of the plot of ln(A/A−X) vs. reaction time as compared to the first order rate line and shown in FIG. 3. In the expression ln(A/A−X), X is the weight % of converted ADN at time, t, and A is the weight % (usually 100) of the ADN at time 0 and ln denoted the natural logarithm.

EXAMPLE 7

The experimental continuous run of Example 2 was repeated using the activated catalyst of Example 6.

Figure 4:
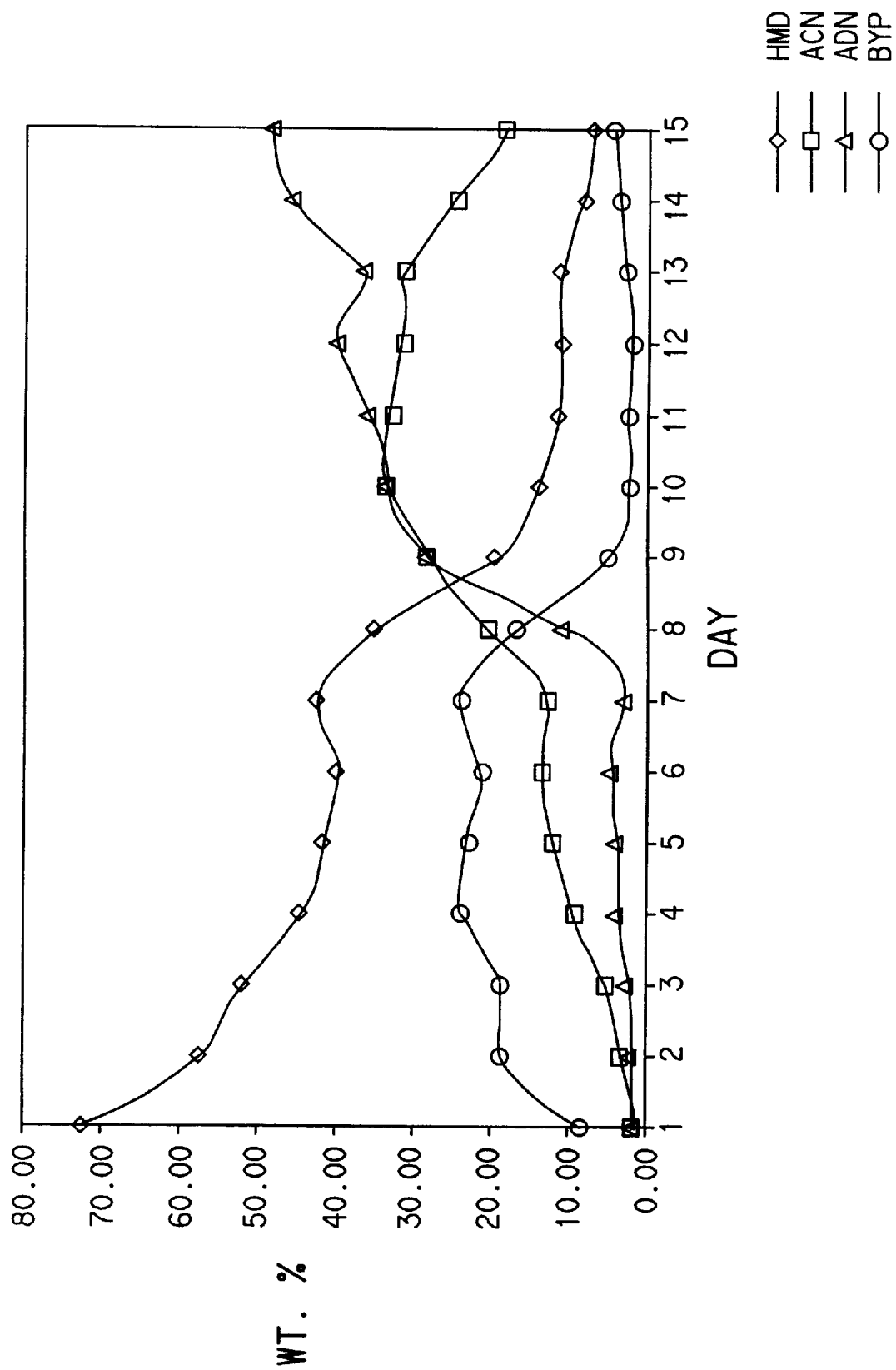
FIG. 4 shows the product distribution of the unstable catalyst of Example 7.

The results of this second run are shown graphically in FIG. 4 and indicate the poor catalyst stability.

EXAMPLE 8

An alloy containing by weight 60 parts aluminum, 24 parts iron, 15 parts cobalt, and 1 part nickel was prepared and converted to an active Raney metal type catalyst by treatment with aqueous sodium hydroxide as described in Example 1.

ADN was hydrogenated in the presence of this catalyst following the procedure of Example 2. Reaction conditions of 75° C. and 500 psig (3.78 MPa) hydrogen pressure were maintained until hydrogen uptake was 115 psig as measured from a 500 ml hydrogen supply reservoir. The total reaction time was 303 minutes at which time ADN conversion was 91%. At 62% ADN conversion, 42% ACN and 4% HMD had formed along with 6% byproducts. No catalyst deactivation was observed as indicated by a stable reaction rate following the first order rate line for disappearance of ADN. This is shown by the straight line plot of ln(A/A−X) vs reaction time. The first order reaction rate constant was 0.473 hr.$^{-1}$

EXAMPLE 9

The following Table illustrates the use of catalyst of the present invention in the hydrogenation of ADN. All reactions were run at 100° C., and except for sample A, the total pressure was 2000 psig (13.78 MPa) (the sum of ammonia and hydrogen partial pressures). Sample A was run at 1000 psig total pressure (6.89 MPa).

TABLE

| Sample | Alloy Composition* | % Conv. ADN | Dist. of Products HMD/N112/ADN | Reaction Rate** gADN/gCat/hr |
|---|---|---|---|---|
| A | $Al_{54}Fe_{38}Co_5Ni3$ | 67 | 12/55/33 | 3.8 |
| B | $Al_{60}Fe_{28}Co_{10}Ni_1$ | 81 | 20/56/19 | 11.5 |
| C | $Al_{60}Fe_{35}Co_5$ | 43 | 3/22/57 | 3.4 |
| D | $Al_{40}Fe_{60}$ | 2 | | |
| E | $Al_{54}Fe_{38}Co_5Ni3$ | 54 | 4/41/46 | 8.5 |

*Weight ration of metals in alloy
**Rate of hydrogenation measured as the grams of ADN produced per gram of catalyst per hour.

The data in the table illustrates the use of the catalysts at pressures up to 2000 psig. The impurities produced in the product mix of the above reactions was measured polarographically. For the catalysts of the present invention these impurities were about 5 times less on average than the impurities produced by a commercial Raney nickel catalyst, Raney nickel 2400 and about 8 times less on average than the level of impurities produced by Raney cobalt 2724. Both of these commercial catalysts are available from W. R. Grace, Davison Chemical Division, Chattanooga, Tenn.

The following Examples illustrate the use and activity of metals other than nickel as the third metal in the catalyst compositions of the present invention. All metals of Group VIII of the Periodic Table may be used in the present invention and provide the benefit of the present invention, but as the Examples below show not all known promoters for Raney catalysts produce acceptable activity when combined with iron and cobalt.

EXAMPLE 10

An alloy containing by weight 60 parts aluminum, 30 parts iron, 9 parts cobalt and one part rhodium was prepared and converted to an active Raney iron catalyst by treatment with aqueous sodium hydroxide as described in Example 1.

ADN was hydrogenated in the presence of this catalyst following the procedure of Example 2. Reaction conditions of 75° C. and 512 psig (3.53 MPa) hydrogen pressure were maintained until hydrogen uptake was 128 psig as measured from a 500 ml hydrogen supply reservoir. The total reaction time was 78 minutes at which time ADN conversion was 96%. At 82% ADN conversion, 55% ACN and 8% HMD had formed along with 11% byproducts. No catalyst deactivation was observed as indicated by a stable reaction rate following the first order rate line for disappearance of ADN. The first order reaction rate constant was 2.813 $hr^{-1}$.

EXAMPLE 11

An alloy containing by weight 60 parts aluminum, 30 parts iron, 9 parts cobalt and one part ruthenium was prepared and converted to an active Raney iron catalyst by treatment with aqueous sodium hydroxide as described in Example 1.

ADN was hydrogenated in the presence of this catalyst following the batch procedure of Example 2. Reaction conditions of 75° C. and 509 psig (3.51MPa) hydrogen pressure were maintained until hydrogen uptake was 155 psig as measured from a 500 ml hydrogen supply reservoir. The total reaction time was 231 minutes. At 87% ADN conversion, 52% ACN, 8% HMD and 9% byproducts had formed. No catalyst deactivation was observed as indicated by a stable reaction rate following the first order rate line for disappearance of ADN The first order rate constant was 1.165 $hr^{-1}$.

EXAMPLE 12

An alloy containing by weight 60 parts aluminum, 30 parts iron, 9 parts cobalt, 0.9 part platinum and 0.1 part rhodium was prepared and converted to an active Raney iron catalyst by treatment with aqueous sodium hydroxide as described in Example 1.

ADN was hydrogenated in the presence of this catalyst following the procedure of Example 2. Reaction conditions of 75° C. and 507 psig (3.49MPa) hydrogen pressure were maintained until hydrogen uptake was 139 psig (0.96 MPa) as measured from a 500 ml hydrogen supply reservoir. The total reaction time was 305 minutes at which time the ADN conversion was 99%. At 84% ADN conversion, 46% ACN and 8% HMD had formed along with 10% byproducts. No catalyst deactivation was observed as indicated by a stable reaction rate following the first order rate line for disappearance of ADN. The first order rate constant was 0.794 $hr^{-1}$.

EXAMPLE 13

The following alloys were prepared and converted to Raney iron catalysts by treatment with aqueous sodium hydroxide as described in Example 1:

| | Aluminum | Iron | Cobalt | Third Metal, parts | |
|---|---|---|---|---|---|
| (1.) | 60 parts | 30 parts | 9 parts | Molybdenum, | 1 |
| (2.) | 60 parts | 30 parts | 9 parts | Chromium, | 1 |
| (3.) | 60 parts | 30 parts | 9 parts | Zirconium, | 1 |
| (4.) | 60 parts | 30 parts | 9 parts | Titanium, | 1 |

ADN was treated with hydrogen at 75° C. to 90° C. and 500 psig (3.45 MPa) hydrogen pressure with each of the activated Raney catalysts from the above alloys. No hydrogen uptake occurred with any of these catalysts.

What is claimed is:

1. A Raney iron catalyst comprising iron, cobalt, a third metal wherein the third metal is selected from the group consisting of nickel, rhodium, ruthenium, palladium, platinum, osmium, and iridium or a combination of any of these metals and wherein the concentration of the iron in the catalyst on a dry basis is at least 30% but not more than about 70% by weight; the concentration of the cobalt in the catalyst on a dry basis is from at least 10 to 40% by weight; the content of the third metal in the catalyst on a dry basis is from about 1 to not more than 6% by weight.

2. A Raney iron catalyst comprising iron, cobalt, and nickel, wherein the concentration of the iron in the catalyst on a dry basis is at least 30% but not more than about 70% by weight; the concentration of the cobalt in the catalyst on a dry basis is from at least 10 to 40% by weight; and the content of the nickel in the catalyst on a dry basis is from about 1 to not more than 6% by weight.

3. The catalyst of claim 2 wherein the concentration of the iron is about 50% by weight; the concentration of the cobalt from 5 to about 15% by weight; the concentration of the nickel is not more than about 4% by weight.

4. The catalyst of claim 2 wherein the concentration of the iron is about 50% by weight; the concentration of the cobalt is from about 9 to 15% by weight; the concentration of the nickel is not more than about 4% by weight.

5. The catalyst of claim 3 wherein the concentration of nickel is about 2%.

6. A process for the hydrogenation of unsaturated organic compounds comprising contacting the unsaturated organic compound with a Raney iron catalyst according to claim 1 in the presence of hydrogen at a reaction pressure of from about 50 to about 2000 psig (0.345 to 13.78 MPa) and a reaction temperature from about 25 to about 150° C.

7. The process of claim 6 wherein the unsaturated organic compound is selected from the group consisting of olefins, acetylenes, ketones, aldehydes, amides, carboxylic acids, esters of carboxylic acids, nitro compounds, nitrites, and imino compounds.

8. The process of claim 6 wherein the unsaturated organic compound is a nitrile.

9. The process of claim 8 wherein the reaction pressure is from about 50 to about 2000 psig (0.345 to 13.78 MPa) and a reaction temperature of from about 60 to about 80° C.

10. The process of claim 6 wherein the process is continuous.

11. The process of claim 6 wherein the process is batch or semi-batch.

12. The process of claim 8 wherein the nitrile is adiponitrile.

13. A process for the hydrogenation of unsaturated organic compounds comprising contacting the unsaturated organic compound or contacting the unsaturated organic compound in the presence of a solvent with a Raney iron catalyst according to claim 2 in the presence of hydrogen at a reaction pressure of from about 50 to about 2000 psig (0.345 to 13.78 MPa) and a reaction temperature of from about 25 to 150° C.

14. The process of claim 13, wherein the concentration of nickel is about 2%.

15. A Raney metal catalyst prepared by treating an alloy of metals with alkali, the alloy comprising from 20 to 50% by weight iron, 3 to 30% by weight cobalt, 0.5 to 3% by weight of a third metal wherein this third metal is selected from the group consisting of nickel, rhodium, ruthenium, palladium, platinum, osmium, iridium and mixtures of any of these metals and wherein the remainder of the mixture is an alkali soluble metal selected from the group consisting of aluminum, zinc, magnesium and silicon.

16. The catalyst of claim 15 wherein the third metal is nickel.

17. The catalyst of claim 15 wherein the concentration of the third metal is from 0.5 to 1.5%.

18. The catalyst of claim 15 wherein the concentration of the third metal is about 1%.

19. The catalyst of claim 15 wherein the concentrations are iron about 24 to 34%, cobalt about 5 to 15% and nickel about 0.5 to 1%.

* * * * *